(12) United States Patent
Hanley

(10) Patent No.: US 8,343,775 B2
(45) Date of Patent: Jan. 1, 2013

(54) METHOD AND DEVICE FOR AFFINITY DIFFERENTIAL INTRAPLEXING

(76) Inventor: Brian P. Hanley, Davis, CA (US)

( * ) Notice: Subject to any disclaimer, the term of this patent is extended or adjusted under 35 U.S.C. 154(b) by 216 days.

(21) Appl. No.: 12/775,387

(22) Filed: May 6, 2010

(65) Prior Publication Data

US 2010/0285978 A1 Nov. 11, 2010

Related U.S. Application Data

(60) Provisional application No. 61/175,841, filed on May 6, 2009.

(51) Int. Cl.
*G01N 33/543* (2006.01)
(52) U.S. Cl. .................................................. 436/518
(58) Field of Classification Search ........................ None
See application file for complete search history.

(56) References Cited

U.S. PATENT DOCUMENTS

| | | | |
|---|---|---|---|
| 6,051,377 A | 4/2000 | Mandecki | |
| 6,268,222 B1 | 7/2001 | Chandler et al. | |
| 6,361,950 B1 | 3/2002 | Mandecki | |
| 6,376,187 B1 | 4/2002 | Mandecki | |
| 6,696,265 B1 | 2/2004 | Spain | |
| 6,916,661 B2 | 7/2005 | Chandler et al. | |
| 6,919,009 B2 | 7/2005 | Stonas et al. | |
| 6,939,720 B2 | 9/2005 | Chandler et al. | |
| 7,033,754 B2 | 4/2006 | Chee et al. | |
| 7,045,049 B1 | 5/2006 | Natan et al. | |
| 7,141,431 B2 | 11/2006 | Chandler et al. | |
| 7,164,533 B2 | 1/2007 | Moon et al. | |
| 7,501,290 B2 * | 3/2009 | Hanley | 436/518 |

* cited by examiner

*Primary Examiner* — Ann Lam
(74) *Attorney, Agent, or Firm* — Temmerman Law Office; Mathew J. Temmerman

(57) ABSTRACT

The present invention provides a method and device for the improvement of intraplexed assays. This improvement is based upon the use of multiple assay chemistries having different affinity constants ($K_A$) for an analyte. The overall assay displays high precision and predictable behavior because ratios between SMPCS-IDGs having different affinity constants ($K_A$) change based on concentration. The advantages of the Applicant's improved system relative to the system of the '290 patent are that the improved system (1) further increases the statistical significance of results from assays applied to single well samples, (2) improves compensation for multiple sources of error, (3) makes possible further increased precision for each analyte, and (4) improves correlation between instruments, even if the instruments have significantly varying responses to an identical stimulus, (4) makes possible improved determination of a margin of error.

20 Claims, 4 Drawing Sheets

METHOD AND DEVICE FOR AFFINITY DIFFERENTIAL INTRAPLEXING

RELATED APPLICATIONS

This application is related to and claims priority from provisional patent application Ser. No. 61/175,841, filed May 6, 2009.

BACKGROUND OF THE INVENTION

1. Field of the Invention

The present invention relates to intraplexed assays, and more particularly to a device and method for improving intraplexed assays to increase precision and predictability of suspended microarray assays.

2. Background

A number of patented technologies exist for use in suspended microarray assays. These include substrate microparticles of various kinds, ways to differentiate between said microparticles, methods of processing the array data, and what is called multiplexing of assays.

There is currently a method for improving assay precision and reliability called intraplexing, as described in U.S. Pat. No. 7,501,290, granted to the present applicant and incorporated herein as if set out in full.

Intraplexing improves upon of the prior art multiplexing techniques by intentionally using more than one particle set targeted at the same analyte within a sample. As disclosed in the '290 patent, intraplexing may employ multiple sets of particles which have different sensitivities to the same analyte in order to better determine analyte concentration. Intraplexing may also employ multiple identically sensitive assays to improve precision in analyte quantification. These techniques can be used to eliminate instrumental variances and make accurate estimates of the true concentration of analytes without necessarily requiring calibration standards be run with every multi-well assay that is performed.

To define intraplexing clearly, and to clarify the Applicant's improvement upon intraplexing, the following terminology is used for purposes of this patent application. A single particle is called an SMP (suspended microarray particle.) A set of microspheres that are all labeled with the same classifier is called an SMPCS (suspended microarray particle category set). An SMPCS is composed of SMPs, which are identically identifiable by use of a flow cytometer or other such devices as are known in the art.

Intraplexing also employs what is called a superset, or SMPCS-IDG (suspended microarray particle category set identical group). In the intraplexing methods disclosed in the '290 patent, an SMPCS-IDG comprises a set of different SMPCSs which are all coated with the same reagent(s) so as to make them identical in sensitivity to the analyte being assayed. In the context of the current invention, an SMPCS-IDG comprises a set of different SMPCSs, which are all coated with the same reagent(s) so as to make them identical in affinity for the analyte being assayed. Bearing this introduction in mind, these terms are discussed in more detail below.

A suspended microarray system uses a population of suspended microarray particles (SMPs), all of which have had their surfaces coated with an assay. After an assay protocol, these SMPs are run through a flow cytometer, which has a flow cell that differentiates individual SMP events as they go by. This flow cell concurrently differentiates individual SMPs, identifies which SMPCS an SMP belongs to, and determines whether the SMP has captured any analyte. Conventionally, most of these SMP-based assays use fluorescent reporter molecules to provide signal, but there are other methods. If multiple SMPCSs are present in a well, then more than one analyte can be assayed simultaneously in the same assay plate well. This is termed multiplexing of assays, and it is a primary selling point for the current generation of suspended microarray systems, such as those sold by Luminex out of Austin, Tex.

Multiplexing suffers from multiple stochastic and non-stochastic sources of error as detailed in the '290 patent. As such, it generally requires replication of samples. Intraplexing as disclosed in the '290 patent overcomes these problems by employing a plurality of SMPCS readings for each assay. Intraplexing also enables statistically significant results to be attained from assays applied to single well samples by generating multiple results from a single well. Intraplexing represents a significant improvement over multiplexing, but there is room for further improvement of the intraplexing method. The current invention seeks to improve upon the previously disclosed intraplexing method by improving precision and reliability of the assay.

It is therefore a first objective of the instant application to improve precision and reliability beyond that disclosed in the '290 patent.

It is a second objective of the instant application to provide a greater degree of redundancy, and hence, of statistical significance, resolving concentration of analytes.

It is a third objective of the instant application to provide an alternative method for improving precision and reliability substantially similar to the '290 patent.

SUMMARY OF THE INVENTION

The present invention provides a method and device for improvement of intraplexed assays. This improvement is based upon the use of multiple assay chemistries that have different affinity constants ($K_A$) for the analyte. The overall assay displays high precision and predictable behavior because ratios between SMPCS-IDGs having different affinity constants ($K_A$) change based on concentration, and the assay configuration is inherently redundant.

This improved method and related device can be applied to any type of suspended array system that uses a plurality of individual readings from particles coupled to an assay. This improved method further compensates for the multiple stochastic and non-stochastic sources of errors that can occur in this type of assay system, and generally improves the accuracy and reliability of the method of the '290 patent.

The advantages of the Applicant's improved system relative to the system of the '290 patent are that the improved system (1) further increases the statistical significance of results from assays applied to single well samples, (2) improves compensation for multiple sources of error, (3) makes possible further increased precision for each analyte, and (4) improves correlation between instruments, even if the instruments have significantly varying responses to an identical stimulus.

BRIEF DESCRIPTION OF THE DRAWINGS

The foregoing aspects and many of the attendant advantages of the invention will become more readily appreciated as the same becomes better understood by reference to the following detailed description, when taken in conjunction with the accompanying drawings, wherein.

DETAILED DESCRIPTION OF THE INVENTION

Figure 1:
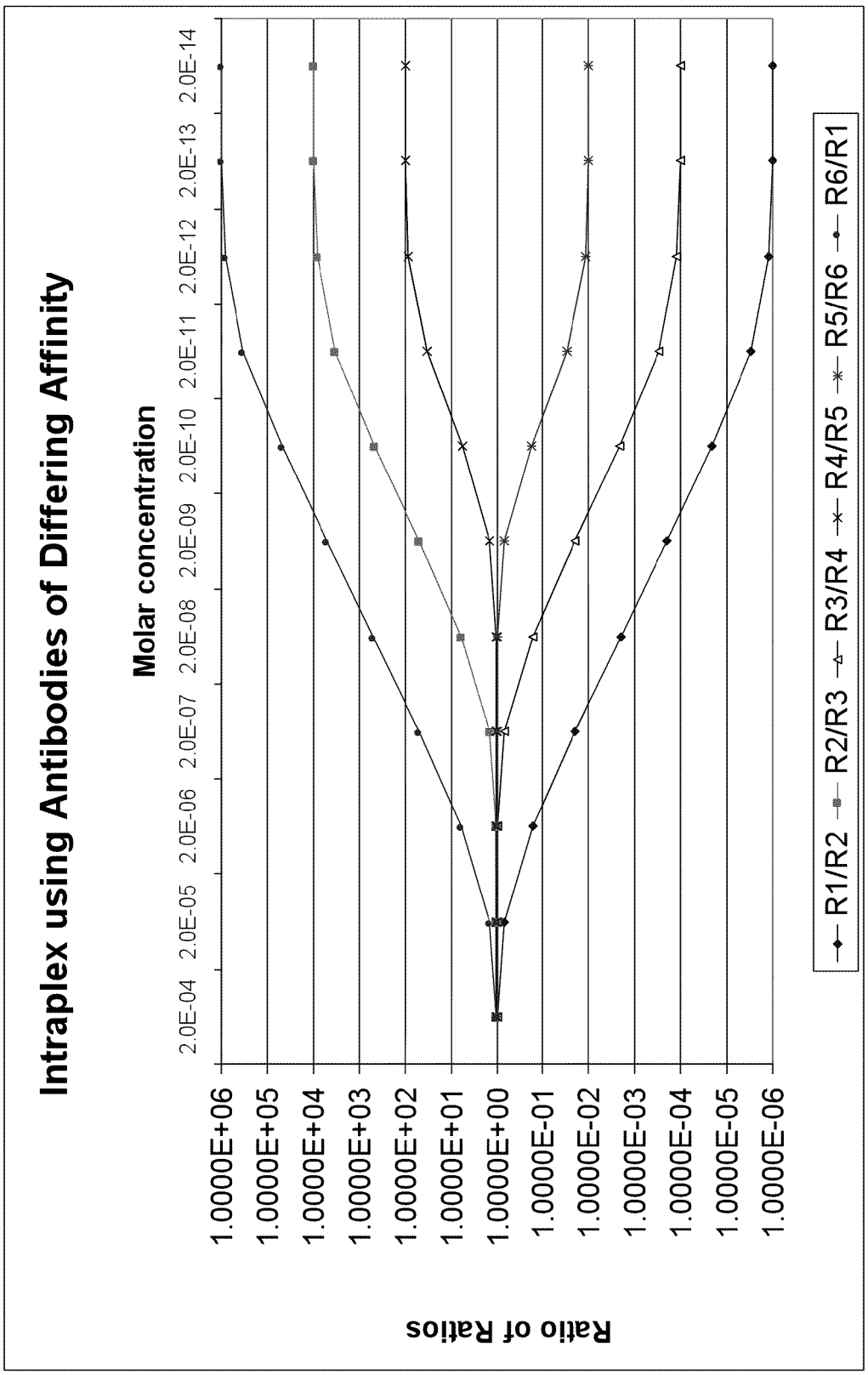
FIG. 1 is a graph depicting simulated results of intraplexing using antibodies of differing affinity, wherein molar concentration is on the X-Axis and a ratio of ratios to the mean average of the set of SMPCS-IDGs is on the Y-Axis. Note that this graph is idealized, and real world antibodies could have ratios to the mean of the set of SMPCS-IDGs that vary such that the ratio of ratios changes from a negative to a positive value and vice versa. This graph shows theoretically attainable maximum and minimum concentrations of analyte likely to be determinable by this method due to the limitations of antibody affinity constants ($K_A$'s) generally attainable. However, higher affinities, should they become possible, should make feasible determination of lower molarity concentrations than shown.

The present invention is an improvement on the Intraplexing Method for Improving Precision of Suspended Microarray Assays as disclosed in U.S. Pat. No. 7,501,290, and incorporated in full herein by reference. With the improved method and related apparatus disclosed in the instant application, it is not necessary that the physical or chemical method of assaying for a specific analyte be identical on each of the suspended microarray intraplex assays. It is only necessary that the end result be a predictable difference in response signal curves for a range of concentrations of analyte due to different affinity constants.

Typically, and as disclosed in the '290 patent, construction of an intraplex requires the use of microparticles having differing levels of sensitivity for the analyte. Typically this is accomplished by coating different SMPCS-IDGs with different quantities of antibodies, but this is not the exclusive method.

In the present application, in place of microparticles having differing levels of sensitivity based on the quantity of assay chemistry present on the microparticles, the improved affinity differential intraplex uses sets of microparticles covered with chemistries that have different affinities for the analyte.

As described above, but summarized here for convenience, a single microparticle is called an SMP (suspended microarray particle). One set of microparticles is referred to as an SMPCS (suspended microarray particle category set). An intraplex superset is referred to as an SMPCS-IDG (suspended microarray particle category set—identical group), and may optionally be referred to as a "bead set". In the instant application, an SMPCS-IDG comprises a set of different SMPCSs, which have assay chemistry such that each SMPCS in the SMPCS-IDG has identical affinity for the analyte. The assay chemistry on different SMPCS-IDGs has antibodies or some other chemistry (generally hydrogen bonding, electrostatic interactions, hydrophobic, or Van der Waals forces) with different affinity constants for the analyte (may also be referred to as "ligand"). Because the affinity of the SMPs in the different SMPCS-IDGs is different, the reactions proceed at different rates to different end points. Thus the ratios between the response curves for different SMPCS-IDGs having different affinities for the analyte (e.g. SMPCS-IDGs coated with different antibodies) should in a zero noise environment not be constant. In fact, the ratios should vary continuously over a wide range of concentrations. Around 1.0E-12 molarity is the preferred limit of differentiation with antibodies that are likely to exist, although other limits are not outside the scope of this invention.

In an exemplary embodiment of the invention, m (where m is greater than or equal to 2 SMPCS-IDGs are used, wherein each SMP has a method of categorization into an SMPCS. Particles in each of the m SMPCS-IDGs must have an assay chemistry that has a significant difference in affinity constant for the target analyte, for example different antibodies. The affinity constant $K_A$ is assumed to apply to non-covalent binding, and is defined below in Equation 1

$$K_A = \frac{[SL]}{[S][L]} \quad \text{Equation 1}$$

In Equation 1, S is the concentration of assay binding sites, L is the concentration of the ligand, SL is the complex of assay binding site with ligand, and $K_A$ is the affinity constant. In a preferred embodiment the assay binding sites are antibodies, although this is not required.

Turning now to FIG. 1, a sample graph modeling the range of an affinity differential intraplexing assay without noise is shown. This graph shows the simulated results for a sample assay based on the affinity constants shown in table 1 for a range of molarities of the analyte. It is also noted that ratios could go from positive to negative if $K_A$ response curves cross.

TABLE 1

| Bead set (SMPCS-IDG) | $K_A$ |
|---|---|
| I1 | 1.0000E+05 |
| I2 | 1.0000E+11 |
| I3 | 1.0000E+07 |
| I4 | 1.0000E+11 |
| I5 | 1.0000E+09 |
| I6 | 1.0000E+11 |

This exemplary graph shown in FIG. 1 depicts the use of ratios of ratios to the mean of the entire set of responses. In this method of analysis, the first step is to calculate ratios to the mean as disclosed in the '290 patent (essentially the ratio of the measured response of an individual SMPCS-IDG to the mean measured response of all SMPCS-IDGs). Subsequently, these ratios to the mean are used to create ratios to each other. The choice of ratios of ratios is arbitrary, and appropriate ratios of ratios are chosen so as to optimize differentiation of concentration of analyte.

As can be seen from the example graph of FIG. 1, by use of SMPCS-IDGs with differing affinities for the analyte in an intraplex assay, the concentration of the analyte can be determined with a high degree of precision and reliability. This may be accomplished by use of ratios to ratios of the mean, or by other analytical techniques apparent to one of skill in the art. The response readings generated by the affinity differential intraplexing method may be analyzed manually, by spreadsheet, by software, or by other techniques to generate a concentration reading for the analyte.

Figure 2:
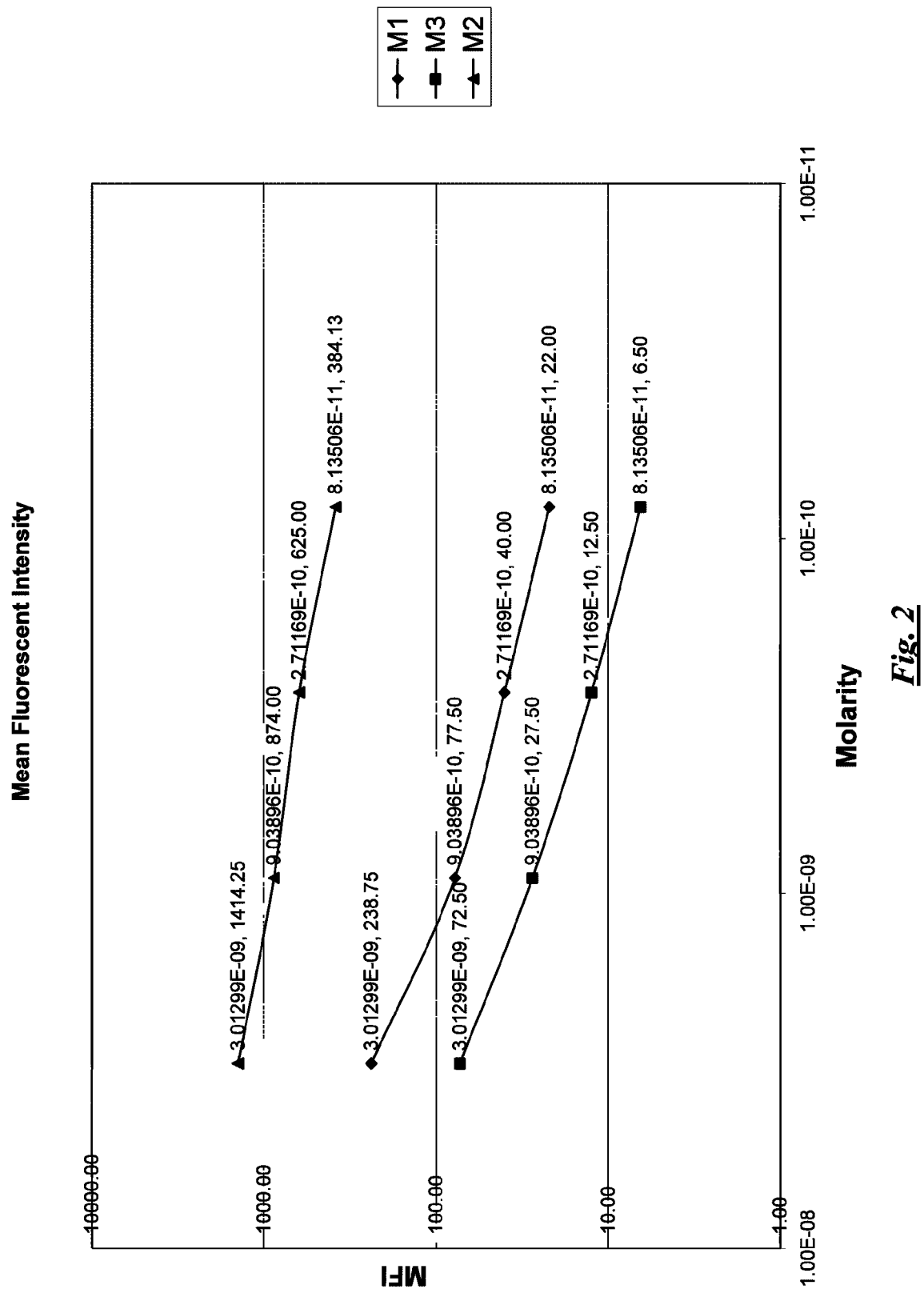
FIG. 2 is a graph showing Mean Fluorescent Intensity on the Y axis and molarity on the X axis for three SMPCS-IDGs.

To further clarify real world use of this method, FIG. 2, shows a sample graph of the raw response curves for three SMPCS-IDGs, M1, M2 and M3, each with differing $K_A$. In this figure molar concentration decreases from left to right, and has a low end sensitivity of just below $10^{-10}$ molar. The values on the Y axis are fluorescent intensity. What is of interest is noting that the shapes of the curves are different on a log scale in the Y axis. The range of sensitivity could extend to $10^{-12}$ molar or better in a perfected system.

Figure 3:
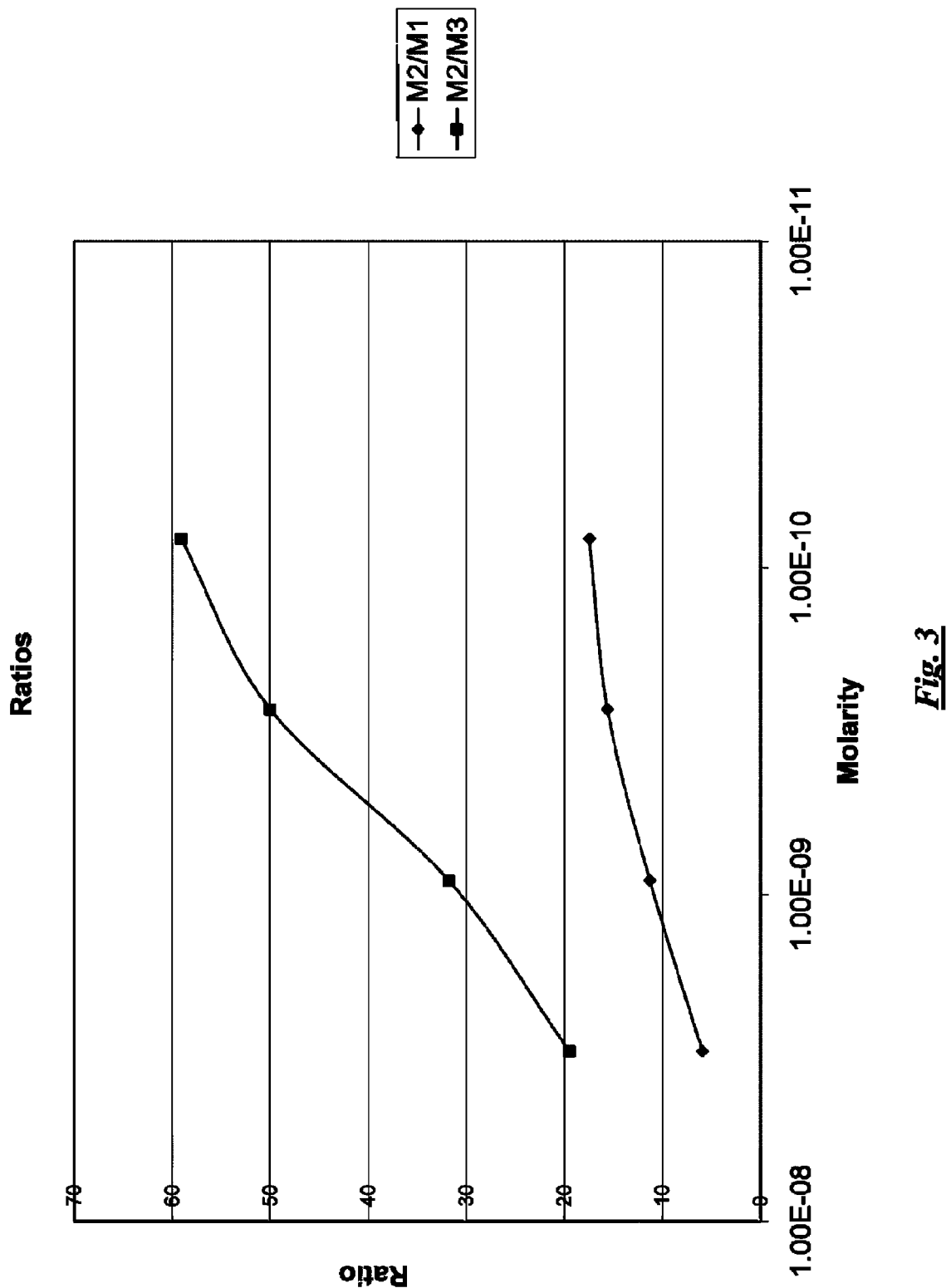
FIG. 3 is a first graph showing fluorescent intensity on the Y axis and molarity on the X axis for three SMPCS-IDGs.

In FIG. 3 is shown a sample graph of the ratios of M2 to M1 and M3 (equivalent to ratio of ratios). Note that depending on choice of the affinity constants for the chosen sets ($K_A$) there may not always be one unique ratio for a given molarity. However, even in these cases what is most of interest is that the ratios can still be useful toward the low end of their detection range, as this is the most problematic area of range to verify in these assays. In the region of the graph where the ratio of ratios is for a high concentration, the simpler method of use of a titration curve can be used. In the lower region of concentration that is most problematic, this method presents an alternative cross-validation of concentration, and a way to estimate a margin of error. It is expected that a designer will usually choose affinity constants that have curves that will generate ratios in accordance with their needs.

Figure 4:
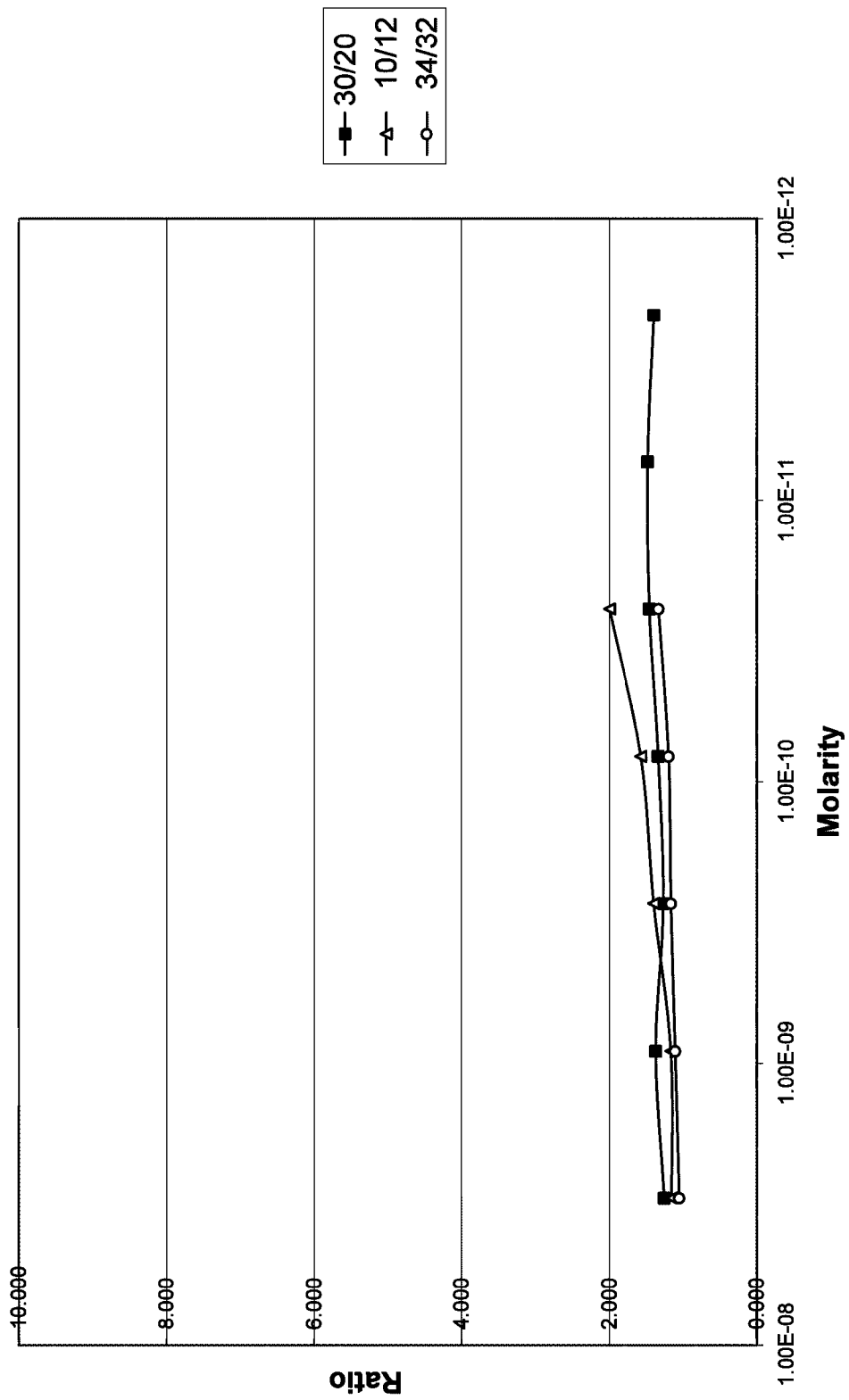
FIG. 4 is a graph a second graph showing fluorescent intensity on the Y axis and molarity on the X axis for three SMPCS-IDGs.

In FIG. 4 is shown a graph of the ratios of identical $K_A$ sets to each other where the sensitivity has been set at a minor degree of difference. This graph is shown to demonstrate that the method described in the instant patent is superior and does exist.

At all concentrations this method can be used to verify that the titration curve results agree with the ratio results. Where used in this way, the instant application provides a method of determining a margin of error by comparing results by titration curve to the method of the instant application.

In use, the invention disclosed herein has application to suspended microarrays and flow cytometry and allows more accurate measurements and better determination of margin of error, to be made by use of flow cytometers. The object of this greater degree of accuracy can allow these inexpensive assays to be used in FDA approved diagnostics which can yield large cost savings.

One skilled in the art will appreciate that the present invention can be practiced by other than the preferred embodiments, which are presented for purposes of illustration and not of limitation. Therefore, the foregoing is considered as illustrative only of the principles of the invention.

I claim:

1. A method for improving the statistical significance of readings from a single sample, the method comprising:
    a) placing a first assay on a microparticle media for reading by an instrument, the first assay comprising:
        i) m number of SMPCS-IDG assays targeted at a common analyte;
        ii) wherein each said SMPCS-IDG assay is designed to exhibit a different response curve to said common analyte based on a difference in affinity constant to the analyte;
        iii) wherein each said SMPCS-IDG assay comprises n number of SMPCS assays;
        iv) wherein each said SMPCS assay is designed to have an affinity to said common analyte and wherein the affinity of each SMPCS-IDG is identical;
        v) wherein m is an integer of at least 2 and n is an integer of at least 1;
    b) obtaining an SMPCS reading from each said SMPCS assay in each said SMPCS-IDG, wherein there are n number of SMPCS readings for each of said m number of SMPCS-IDG assays.

2. The method according to claim 1 further comprising the step of removing outlier values from said n number of SMPCS readings if the outlier values are present.

3. The method according to claim 2 further comprising the step of taking one of either an arithmetic mean average, geometric mean average, harmonic mean average, or quadratic mean average of said n number of SMPCS readings to generate m means of the sets of n SMPCSs, one mean of the set of n SMPCSs for each SMPCS-IDG assay.

4. The method according to claim 3 further comprising the step of taking one of either an arithmetic mean average, geometric mean average, harmonic mean average, or quadratic mean average of said m means of the sets of n SMPCSs to calculate a mean of the set of m SMPCS-IDGs.

5. The method according to claim 4 further comprising the step of determining m ratios of each of said m means of the sets of n SMPCSs to said mean of the set of m SMPCS-IDGs.

6. The method according to claim 4 further comprising the step of determining m ratios of said mean of the set of m SMPCS-IDGs to each of said m means of the sets of n SMPCSs.

7. The method according to claim 5 further comprising the step of determining o ratios of ratios, each consisting of: ratios of one of said m ratios of each of said m means of the sets of n SMPCSs to said mean of the set of m SMPCS-IDGs to another one of said m ratios of each of said m means of the sets of n SMPCSs to said mean of the set of m SMPCS-IDGs.

8. The method of claim 5, further comprising the steps of:
    a) creating a calibration dataset by running multiple samples of known concentrations of said common analyte at different concentrations and
    b) recording for each of said multiple samples of known concentrations of said common analyte at least one reading selected from the group of:
        i) said known concentration of said common analyte;
        ii) said SMPCS readings from each SMPCS assay;
        iii) said m number for said SMPCS-IDGs in the first assay;
        iv) said n number for the SMPCSs in each SMPCS-IDG in the first assay;
        v) a list of classifiers for each SMPCS-IDG assay; or
        vi) o ratios of ratios.

9. The method according to claim 8, wherein said m ratios are compared to predetermined calibration dataset ratios to estimate a probable range of concentration of said analyte by comparing the range of said m ratios to the ranges of said m ratios in the calibration dataset.

10. The method according to claim 8, wherein said o ratios of ratios are compared to predetermined calibration dataset ratios to estimate a probable range of concentration of said analyte by comparing the range of said m ratios of ratios to the ranges of said o ratios in the calibration dataset.

11. The method according to claim 8, wherein said m ratios and o ratios are compared to predetermined calibration dataset ratios and to titration curve data for an instant assay to estimate a probable margin of error for the assay.

12. The method of claim 6, further comprising the steps of:
    a) creating a calibration dataset by running multiple samples of known concentrations of said common analyte at different concentrations and
    b) recording for each of said multiple samples of known concentrations of said common analyte at least one reading selected from the group of:
        i) said known concentration of said common analyte;
        ii) said SMPCS readings from each SMPCS assay;
        iii) said m number for said SMPCS-IDGs in the first assay;
        iv) said n number for the SMPCSs in each SMPCS-IDG in the first assay;
        v) a list of classifiers for each SMPCS-IDG assay; or
        vi) o ratios of ratios.

13. The method according to claim 12, wherein said m ratios are compared to predetermined calibration dataset ratios to estimate a probable range of concentration of said analyte by comparing the range of said m ratios to the ranges of said m ratios in the calibration dataset.

14. The method according to claim 12, wherein said o ratios of ratios are compared to predetermined calibration dataset ratios to estimate a probable range of concentration of said analyte by comparing the range of said m ratios of ratios to the ranges of said o ratios in the calibration dataset.

15. The method according to claim 12, wherein said m ratios and o ratios are compared to predetermined calibration dataset ratios and to titration curve data for an instant assay to estimate a probable margin of error for the assay.

16. The method of claim 7, further comprising the steps of:
   a) creating a calibration dataset by running multiple samples of known concentrations of said common analyte at different concentrations and
   b) recording for each of said multiple samples of known concentrations of said common analyte at least one reading selected from the group of:
      i) said known concentration of said common analyte;
      ii) said SMPCS readings from each SMPCS assay;
      iii) said m number for said SMPCS-IDGs in the first assay;
      iv) said n number for the SMPCSs in each SMPCS-IDG in the first assay;
      v) a list of classifiers for each SMPCS-IDG assay; or
      vi) o ratios of ratios.

17. The method according to claim 16, wherein said m ratios are compared to predetermined calibration dataset ratios to estimate a probable range of concentration of said analyte by comparing the range of said m ratios to the ranges of said m ratios in the calibration dataset.

18. The method according to claim 16, wherein said o ratios of ratios are compared to predetermined calibration dataset ratios to estimate a probable range of concentration of said analyte by comparing the range of said m ratios of ratios to the ranges of said o ratios in the calibration dataset.

19. The method according to claim 16, wherein said m ratios and o ratios are compared to predetermined calibration dataset ratios and to titration curve data for an instant assay to estimate a probable margin of error for the assay.

20. An improved intraplex assay method comprising:
   a) providing m different SMPCS-IDG assays targeted at a common analyte, wherein each said SMPCS-IDG assay has a different affinity constant for the said analyte, and wherein each SMPCS-IDG assay comprises n number of SMPCS assays, and wherein m is an integer of at least 2 and n is an integer of at least 1;
   b) performing an assay protocol wherein the SMPs of said SMPCS-IDGs capture said analyte and said capture's behavior is determined by the affinities of said SMPCS-IDGs;
   c) performing a reading procedure wherein each SMP is detected and categorized individually; and
   d) analyzing the results of said reading procedure so as to quantitatively measure said analyte.

* * * * *